United States Patent
Yang

(10) Patent No.: US 12,048,614 B2
(45) Date of Patent: Jul. 30, 2024

(54) FUNCTIONAL DIAPER

(71) Applicant: KOREA JINTECH, Incheon (KR)

(72) Inventor: Kidae Yang, Incheon (KR)

(73) Assignee: KOREA JINTECH, Incheon (KR)

( * ) Notice: Subject to any disclaimer, the term of this patent is extended or adjusted under 35 U.S.C. 154(b) by 816 days.

(21) Appl. No.: 17/044,810

(22) PCT Filed: Mar. 6, 2019

(86) PCT No.: PCT/KR2019/002556
§ 371 (c)(1),
(2) Date: Oct. 1, 2020

(87) PCT Pub. No.: WO2019/182266
PCT Pub. Date: Sep. 26, 2019

(65) Prior Publication Data
US 2021/0353474 A1     Nov. 18, 2021

(30) Foreign Application Priority Data
Mar. 19, 2018  (KR) .......................... 10-2018-0031569

(51) Int. Cl.
*A61F 13/495* (2006.01)
(52) U.S. Cl.
CPC .... *A61F 13/495* (2013.01); *A61F 2013/4951* (2013.01)
(58) Field of Classification Search
CPC .................. A61F 13/495; A61F 13/505; A61F 13/00557; A61F 13/49; A61F 13/53;
(Continued)

(56) References Cited

U.S. PATENT DOCUMENTS 5,330,459 A * 7/1994 Lavon .................. A61F 13/495
604/385.12
6,440,114 B1 * 8/2002 Bast ..................... A61F 13/495
604/385.01
(Continued)

FOREIGN PATENT DOCUMENTS

JP     2000-126215 A    5/2000
KR     20-0355208 Y1    7/2004
(Continued)

OTHER PUBLICATIONS

KR Office Action dated May 14, 2018 as received in Application No. 10-2018-0031569.
(Continued)

*Primary Examiner* — Benjamin J Klein
*Assistant Examiner* — Gabriella E Burnette
(74) *Attorney, Agent, or Firm* — Maschoff Brennan

(57) ABSTRACT

The present invention relates to a functional diaper, which can be worn by a baby or a patient and comprises a body having, therein, an excrement storage part, which is a space for gathering excrement, wherein the upper part of the excrement storage part has an excrement entrance that allows excrement to enter therein and exit therefrom. The present invention allows urine or excrement to be immediately and separably stored in a separate space of the diaper immediately after coming out of the anus such that there is little odor and excrement does not come in contact with the skin, and thus the present invention prevents bedsores and the like and is remarkably clean and sanitary.

1 Claim, 1 Drawing Sheet

(58) Field of Classification Search
CPC .............. A61F 13/15; A61F 2013/4953; A61F 2013/4956; A61F 2013/4951; A61F 2013/4958; A61F 2013/1513; A61F 2013/00978; A61F 2013/00557; A61F 5/4401; A61F 5/496; A61F 13/66; A61F 13/665; A47K 11/04; A47K 11/11
See application file for complete search history.

(56) References Cited

U.S. PATENT DOCUMENTS

| | | | | |
|---|---|---|---|---|
| 7,175,613 | B2* | 2/2007 | Sugiyama | A61F 13/495 604/385.01 |
| 10,070,998 | B2* | 9/2018 | Herron | A61F 13/51458 |
| 2014/0188067 | A1* | 7/2014 | Herron | A61F 13/513 604/385.01 |
| 2016/0229595 | A1* | 8/2016 | Connolly | B65D 33/25 |
| 2020/0246178 | A1* | 8/2020 | O'Hamill | A61F 5/449 |
| 2023/0181384 | A1* | 6/2023 | Matthews | A61F 13/58 604/367 |

FOREIGN PATENT DOCUMENTS

| | | |
|---|---|---|
| KR | 10-0456504 B1 | 1/2005 |
| KR | 10-2011-0040264 A | 4/2011 |
| KR | 20-0458014 | 1/2012 |
| KR | 10-1127945 B1 | 3/2012 |
| KR | 20-0459495 Y1 | 3/2012 |
| KR | 10-1914781 B1 | 11/2018 |

OTHER PUBLICATIONS

KR Decision to Grant Dated Jul. 27, 2018 as received in Application No. 10-2018-0031569.

* cited by examiner

FUNCTIONAL DIAPER

TECHNICAL FIELD

The present disclosure relates to a functional diaper, and more particularly, to a functional sanitary diaper including a body having, therein, an excrement storage part defining a space for collecting excrement, wherein an upper part of the excrement storage part has an excrement entrance allowing the excrement to pass therethrough such that urine or excrement is separated and stored in a separate space of the diaper immediately after exiting the anus or the like. The functional diaper is clean and hygienic so as to cause little smell and prevent excrement from touching the skin and causing pressure sores or the like.

BACKGROUND ART

In general, babies or patients wear diapers to contain waste. The diaper is convenient to wear or has various functions for hygiene.

As an example, Korean Utility Model No. 20-0458014 discloses a diaper formed of a waterproof material, including a cover having an outer cover provided with a pocket formed on one side thereof and an inner cover coupled to the outer cover and formed of a cotton material; an absorption pad detachably coupled to the inside of the cover; a plurality of sub-absorption pads disposed from a middle portion to one end portion of the absorption pad in an overlapping manner and detachably coupled to the absorption pad, the sub-absorption pads being detachably coupled to each other; an excrement detection sensor detachably coupled to the inner cover and disposed on an opposite side of the absorption pad to detect the excrement on the absorption pad; a urine detection sensor detachably coupled to the inner cover and disposed to correspond to the sub-absorption pads to detect urine on the sub-absorption pads; and a controller inserted into the pocket of the outer cover and connected to the excrement detection sensor and the urine detection sensor to receive detection information transmitted from the excrement detection sensor and the urine detection sensor to generate an alarm sound when the detection information exceeds a preset value, wherein tissues are coupled to both ends of the outer cover, respectively in a rolled state such that the tissues can be unrolled for use. When a user defecates, the tissues can be used to wipe off the excrement on the user's body and then to cover the excrement on the absorption pad while being coupled to the outer cover. The document also discloses that the excrement detection sensor and the urine detection sensor detect one of change in temperature, change in smell, and change in weight of the absorption pad or the sub-absorption pads.

Also, Korean Patent No. 10-1127945 discloses a functional diaper including an absorption layer formed of pulp paper to absorb liquid, a lining fixedly attached to one surface of the absorption layer and formed of pure cotton or 60 thread cotton, a vinyl coating layer formed by coating the opposite surface of the absorption layer with a synthetic vinyl resin to a predetermined thickness, and a composition layer made of a material capable of generating far infrared light and formed on the one surface of the absorption layer to a predetermined thickness, wherein a thermal insulation and through-hole layer 3 is provided between the lining 2 and the composition layer 13. The document discloses that the thermal insulation and through-hole layer 3 is made of cashmere or a non-woven fabric having a function of maintaining a constant temperature, and is attached and fixed to the composition layer 13.

Urine treatment devices and excrement treatment devices employing the above-described conventional techniques have been mechanically applied to the elderly and patients. However, under a practical environment, whether the devices are in use is almost unclear. Further, such devices are very inconvenient and expensive.

Conventional diapers are not hygienic because the space between the diaper and the human body is very narrow and thus the groin, navel, and even hips may get excrement. In particular, for women, the anus is positioned very close to the vagina, but conventional diapers frequently have a risk of infiltration of excrement into the vagina and raise issues regarding hygiene.

DISCLOSURE

Technical Problem

Therefore, the present disclosure has been made in view of the above problems, and it is one object of the present disclosure to provide a clean and hygienic functional diaper capable of separating and storing urine or excrement exiting the anus in a separate space of the diaper to minimize smell and prevent the excrement from touching the skin and causing pressure sores.

Technical Solution

In accordance with one aspect of the present disclosure, provided is a functional diaper wearable by a baby or a patient, including a body 100 provided therein with an excrement storage part 10, an upper portion of the excrement storage part 10 being provided with an excrement outlet 20 allowing excrement to pass therethrough.

Advantageous Effects

According to the present disclosure, excrement or urine is separated and stored in a separate space of the diaper as soon as the urine or excrement exits the anus. Accordingly, little smell may be generated. In addition, since the excrement does not touch the skin, pressure sores may be prevented and the diaper may be clean and hygienic.

Figure 1:
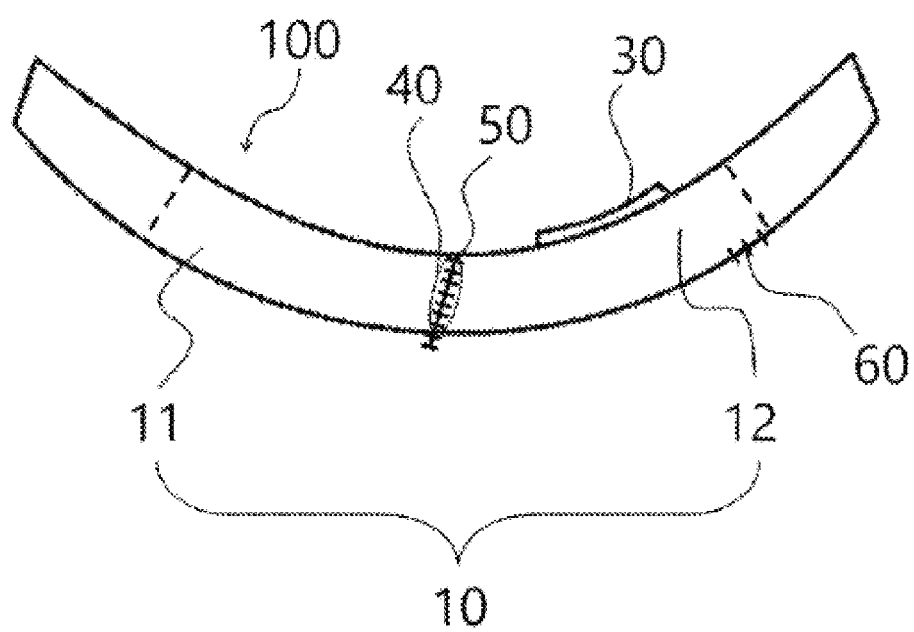
FIG. 1 is a cross-sectional view of a functional diaper according to the present disclosure.

100: Body 10: Excrement storage part 20: Excrement outlet 30: Adhesive band

BEST MODE

The present disclosure is directed to a functional diaper wearable by a baby or a patient, including a body 100 provided therein with an excrement storage part 10. An upper portion of the excrement storage part 10 is provided with an excrement outlet 20 allowing excrement to pass therethrough.

In addition, a disposable adhesive band 30 is adhered to the excrement outlet 20.

MODE FOR INVENTION

Figure 2:
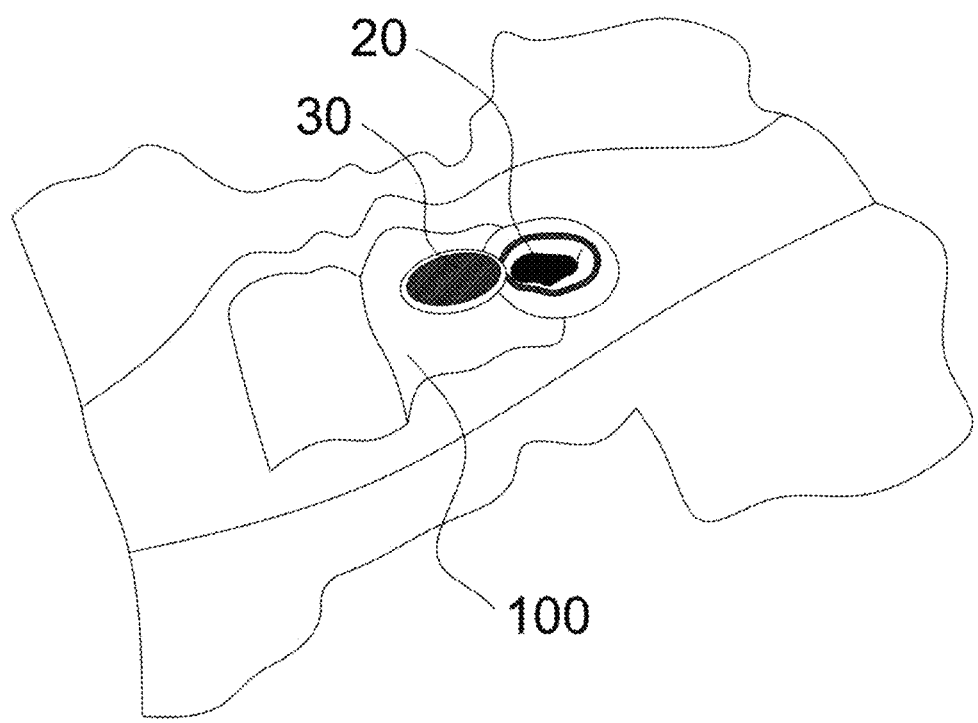
FIG. 2 illustrates the functional diaper according to the present disclosure.

The present disclosure will be described in detail with reference to the accompanying drawings. FIG. 1 is a cross-sectional view of a functional diaper according to the present disclosure, and FIG. 2 illustrates the functional diaper according to the present disclosure.

The band of the present disclosure is wearable by babies or patients and is formed in a rectangular shape like a normal diaper. The band is made of a silicone material that is safe for the human body. It is of a solvent-free type such as acrylic and is composed of a pure material. The band contains silver nanomaterials to have an antibacterial effect. The adhesive band is basically made of a silicone material that is safe for the human body and an acrylic base, the content of which may be determined according to the strength of the adhesive force. In addition, the band maintains antimicrobial properties so as to prevent the propagation of bacteria in the epithelial tissue to ensure safety for the human body and not to degrade adhesiveness.

The inside of the band is left empty to define the excrement storage part 10, which is a space for collecting excrement. Accordingly, the present invention may separate and treat the urine and excrement at once. A disposable adhesive band is adhered to the excrement outlet 20. The adhesive band is removed before use.

The excrement storage part is configured in a dual structure including an upper excrement storage part and a lower excrement storage part, which are connected through a passage. The passage may be opened and closed by a passage waterproofing zipper. Another waterproof zipper is provided to the lower surface of the lower excrement storage part. Accordingly, after excrement is primarily stored in the lower excrement storage part, the storage part can be closed by the passage waterproofing zipper and the upper excrement storage part can be temporarily used. The lower excrement storage part may be opened by the waterproofing zipper on the lower surface of the lower excrement storage part to discharge the stored excrement. Accordingly, both efficiency and convenience may be obtained.

Therefore, according to the present disclosure, excrement or urine is separated and stored in a separate space of the diaper as soon as the urine or excrement exits the anus. Accordingly, little smell may be generated. In addition, since the excrement does not touch the skin, pressure sores may be prevented and the diaper may be clean and hygienic.

INDUSTRIAL APPLICABILITY

The present disclosure relates to a functional diaper wearable by a baby or a patient and capable of separating and storing urine or excrement coming out of the anus in a separate space of the diaper to cause little smell and prevent the excrement from touching the skin and causing pressure sores, thereby maintaining a clean and hygienic condition. Accordingly, the functional diaper has high applicability as a consumer good.

The invention claimed is:

1. A functional diaper wearable by a baby or a patient comprising:
    a body provided therein with an excrement storage part;
    an excrement outlet formed in an upper portion of the excrement storage part to allow excrement to pass therethrough; and
    a disposable adhesive band adhered to the excrement outlet,
    wherein the excrement storage part is configured in a dual structure including an upper excrement storage part and a lower excrement storage part, the upper excrement storage part and the lower excrement storage part being connected through a passage,
    wherein:
    the passage is provided with a passage waterproofing zipper, the passage being opened and closed by the passage waterproofing zipper; and
    the lower excrement storage part is provided with a waterproofing zipper on a lower surface thereof,
    wherein, when the lower excrement storage part is closed by the passage waterproofing zipper after the excrement is primarily stored in the lower excrement storage part, the upper excrement storage part is temporarily used,
    wherein the lower excrement storage part is opened by the waterproofing zipper on the lower surface of the lower excrement storage part to discharge the stored excrement to obtain both efficiency and convenience.

* * * * *